United States Patent
Clayton et al.

(10) Patent No.: US 8,251,228 B2
(45) Date of Patent: Aug. 28, 2012

(54) PROCESS AND APPARATUS FOR ADSORPTIVE BUBBLE SEPARATION

(75) Inventors: Robert L. Clayton, Tuscon, AZ (US);
Stephen N. Falling, Kingsport, TN (US); Jeffrey S. Kanel, Kingsport, TN (US); C. Calvert Churn, III, Kingsport, TN (US)

(73) Assignees: Renewable Algal Energy, LLC, Kingsport, TN (US); Eastman Chemical Company, Kingsport, TN (US)

( * ) Notice: Subject to any disclaimer, the term of this patent is extended or adjusted under 35 U.S.C. 154(b) by 111 days.

(21) Appl. No.: 12/665,211

(22) PCT Filed: Jun. 18, 2008

(86) PCT No.: PCT/US2008/007613
§ 371 (c)(1),
(2), (4) Date: Dec. 17, 2009

(87) PCT Pub. No.: WO2008/156795
PCT Pub. Date: Dec. 24, 2008

(65) Prior Publication Data
US 2010/0181234 A1    Jul. 22, 2010

Related U.S. Application Data

(60) Provisional application No. 60/944,813, filed on Jun. 19, 2007.

(51) Int. Cl.
*B03D 1/14* (2006.01)
*B03D 1/24* (2006.01)
*C02F 1/24* (2006.01)

(52) U.S. Cl. ...... 209/164; 209/170; 210/703; 210/221.2

(58) Field of Classification Search .................. 210/703, 210/221.2; 209/164, 170
See application file for complete search history.

(56) References Cited

U.S. PATENT DOCUMENTS
3,428,175 A    2/1969    Hukki
(Continued)

FOREIGN PATENT DOCUMENTS
AU    2002101010    5/2003
(Continued)

OTHER PUBLICATIONS

Flotation Science and Engineering, pp. 1-44 (K.A. Mattis ed., 1995) Marcel Dekker, New York, NY.
(Continued)

*Primary Examiner* — Thomas M Lithgow
(74) *Attorney, Agent, or Firm* — Phan Law Group PLLC (57) ABSTRACT

Process and apparatus are described for adsorptive bubble separation of hydrophobic particles from liquid dispersions. The process may be used to treat the gas/liquid dispersion after it has been introduced from two or more ducts near the perimeter or from a central duct of the separation vessel. When the gas-liquid-particle dispersion is introduced from a central duct, the rising bubbles are directed by, e.g., a baffle toward the perimeter of the apparatus, where they rise. At the liquid surface, bubbles with attached hydrophobic materials form a floating froth layer, which is directed toward a central froth collection launder. Rising froth at the perimeter pushing the froth bed into the reduced area of the center encourages further coalescence of the bubbles and increases liquid drainage from the froth, thus leading to concentration of the collected materials without the need for complex equipment geometry. Also disclosed is an improvement for froth flotation processes comprising using a vacuum to pull froth and/or collapsed froth into and through the froth collection launder and froth drain line. This improvement assists froth collection because froth can be pulled by suction through the collection system more easily than it can be drained by gravity.

14 Claims, 6 Drawing Sheets

U.S. PATENT DOCUMENTS

| | | | |
|---|---|---|---|
| 3,730,341 A * | 5/1973 | Mames et al. | 209/164 |
| 3,802,569 A * | 4/1974 | Nagahama | 210/219 |
| 3,875,052 A | 4/1975 | Lonchamp et al. | |
| 3,951,805 A | 4/1976 | Dodd | |
| 4,021,303 A | 5/1977 | Nakabayashi | |
| 4,055,491 A | 10/1977 | Porath-Furedi | |
| 4,115,949 A | 9/1978 | Avron et al. | |
| 4,186,094 A * | 1/1980 | Hellberg | 210/221.2 |
| 4,288,319 A * | 9/1981 | Heijs et al. | 209/166 |
| 4,399,028 A | 8/1983 | Kile et al. | |
| 4,425,232 A | 1/1984 | Lawrence et al. | |
| 4,554,390 A | 11/1985 | Curtain et al. | |
| 4,668,382 A | 5/1987 | Jameson | |
| 4,680,314 A | 7/1987 | Nonomura | |
| 4,735,709 A | 4/1988 | Zipperian | |
| 4,800,017 A | 1/1989 | Krishnaswamy et al. | |
| 4,931,291 A | 6/1990 | Kojima et al. | |
| 4,938,865 A | 7/1990 | Jameson | |
| 4,981,582 A | 1/1991 | Yoon et al. | |
| 5,022,984 A | 6/1991 | Pimpley et al. | |
| 5,078,921 A | 1/1992 | Zipperian | |
| 5,167,798 A | 12/1992 | Yoon et al. | |
| 5,167,806 A | 12/1992 | Wang et al. | |
| 5,188,726 A | 2/1993 | Jameson | |
| 5,205,926 A | 4/1993 | Lawrence | |
| 5,240,600 A | 8/1993 | Wang | |
| 5,242,580 A * | 9/1993 | Sury | 208/400 |
| 5,251,764 A | 10/1993 | Niiti et al. | |
| 5,330,913 A | 7/1994 | Nakayama | |
| 5,332,100 A | 7/1994 | Jameson | |
| 5,374,522 A | 12/1994 | Murphy et al. | |
| 5,382,358 A | 1/1995 | Yeh | |
| 5,431,286 A | 7/1995 | Xu et al. | |
| 5,490,924 A | 2/1996 | Macia et al. | |
| 5,626,767 A | 5/1997 | Trampler et al. | |
| 5,651,879 A | 7/1997 | Gonzalez | |
| 5,776,349 A | 7/1998 | Guelcher et al. | |
| 5,897,772 A | 4/1999 | Chiang et al. | |
| 5,910,254 A | 6/1999 | Guelcher et al. | |
| 5,951,875 A | 9/1999 | Kanel | |
| 6,000,551 A * | 12/1999 | Kanel et al. | 209/164 |
| 6,092,667 A | 7/2000 | Steinmuller et al. | |
| 6,328,165 B1 | 12/2001 | Baker et al. | |
| 6,332,980 B1 | 12/2001 | Moorehead | |
| 6,405,948 B1 | 6/2002 | Hahn et al. | |
| 6,524,486 B2 | 2/2003 | Borodyanski | |
| 6,589,785 B1 | 7/2003 | Mullner et al. | |
| 6,832,690 B2 | 12/2004 | Kujawa | |
| 7,108,136 B2 | 9/2006 | Imhof | |
| 2003/0201232 A1 | 10/2003 | Cheyne | |
| 2006/0084165 A1 | 4/2006 | Lee et al. | |

FOREIGN PATENT DOCUMENTS

| | | | |
|---|---|---|---|
| DE | 3101221 A1 * | 8/1982 | |
| DE | 3634903 A1 * | 4/1988 | |
| GB | 2114469 A * | 8/1983 | |
| WO | 2006056018 | 6/2006 | |

OTHER PUBLICATIONS

Adsorptive Bubble Separation Techniques, pp. 1-5 (R. Lemlich ed., 1972) Academic Press, New York, NY.

G.V. Levin et al., "Harvesting of Algae by Froth Flotation," Applied and Environmental Microbiology, vol. 10, pp. 169-175 (1962).

Y. Christi, "Biodiesel from Microalgae," Biotechnology Advances, vol. 25, pp. 294-306 (2007).

"A Look Back at the U.S. Department of Energy's Aquatic Species Program: Biodiesel from Algae," NREL/TP-580-24190, pp. 1-294 (1998).

Olaizola, M., "Commercial Development of Microalgal Biotechnology: From the Test Tube to the Marketplace," Biomolecular Eng., Elsevier, New York, NY, vol. 20, No. 4-6, pp. 459-466 (Jul. 1, 2003).

Molina, Grima E., et al., "Recovery of Microalgal Biomass and Metabolites: Process Options and Economics," Biotechnology Advances, Elsevier Publishing, Barking, GB, vol. 20, No. 7-8, pp. 491-515 (Jan. 1, 2003).

English Abstract of DE 3 634 903 A1 from EPO database (date unavailable).

English Abstract of DE 3 101 221 A1 from EPO database (date unavailable).

* cited by examiner

PROCESS AND APPARATUS FOR ADSORPTIVE BUBBLE SEPARATION

REFERENCE TO RELATED APPLICATION

This application claims priority under 35 U.S.C. §119(e) to U.S. Provisional Patent application 60/944,813, filed on Jun. 19, 2007, the contents of the entirety of which are incorporated herein by this reference.

BACKGROUND

Adsorptive bubble separation (which includes froth flotation, flotation, bubble fractionation, dissolved air flotation, and solvent sublation) is a process in which a molecular, colloidal or particulate material is selectively adsorbed to the surface of gas bubbles rising through a liquid, and is thereby concentrated or separated. A commonly used type of adsorptive bubble separation process is froth flotation wherein the bubble-particle agglomerates accumulate on the liquid surface as a floating froth. The froth with adsorbed (i.e., attached or collected) particles is treated in one of several ways to collapse the froth and isolate the material. See for example, Flotation Science and Engineering, K. A. Mattis, Editor, pages 1 to 44, Marcel Dekker, New York, N.Y., 1995; and Adsorptive Bubble Separation Techniques, Robert Lemlich, Editor, pages 1 to 5, Academic Press, New York, N.Y., 1972.

This important process is commercially utilized in a wide range of applications including: isolation of minerals and metals from an ore-water slurry, dewatering of microalgae, yeast or bacterial cells, removal of oil from water, removal of ash from coal, removal of particles in waste-water treatment streams, purification of drinking water, and removal of ink and adhesives during paper recycling. In most applications, it is necessary to add reagents, known as "collectors", which selectively render one or more of the species of particles in the feed hydrophobic, thereby assisting in the process of collection by the gas bubbles. It is also not unusual to add frothing agents to assist in the formation of a stable froth on the surface of the liquid. The process of admitting these various reagents to the system is known as conditioning. The feed for the adsorptive bubble separation process may be a mixture, dispersion, emulsion, slurry, or suspension of a molecular, colloidal and/or particulate material in a liquid and is referred to hereafter as the liquid-particle dispersion. When the liquid is water, as is usually the case, the feed may be referred to as an aqueous-particle dispersion.

Because of the importance of adsorptive bubble separation processes, there have been many attempts to improve the efficiency and selectivity of particle capture from an aqueous-particle dispersion in order to increase product yield and purity.

U.S. Pat. Nos. 4,668,382, 4,938,865, 5,332,100, and 5,188,726 (the contents of the entirety of each of which are incorporated herein by this reference) disclose an adsorptive bubble separation process and apparatus (commonly known as a "Jameson cell") wherein an aqueous-particle dispersion enters the top of a vertical duct (downcomer) and passes through an orifice plate to form a high velocity, downward facing liquid jet. A gas, usually air introduced into the downcomer headspace, is dispersed into the mixture as the liquid jet impacts a foam column within the downcomer. The volume within the downcomer is referred to as the collection zone wherein most of the particles adsorb to the surface of the bubbles. The resulting gas-liquid-particle dispersion exits through the bottom of the downcomer into the separation zone where the bubbles separate from the tails (water and non-adsorbed materials). In the separation zone, the gas-liquid-particle dispersion has sufficient residence time to allow the tiny bubbles with collected particles to coalesce (combine and enlarge) and rise to the liquid surface forming a particle-rich, floating froth in the froth zone. The froth is collected by allowing it to float outward to the perimeter of the apparatus and overflow into an open launder (collection trough). Provisions are made in these patents to incorporate froth washing in the froth zone by introducing a liquid onto the froth from above thus creating a net downward liquid flow and washing the entrained gangue (undesired solid matter) and non-adsorbed particles away from the froth. This washing produces a purer froth, and therefore a more selective separation. In the design described in these patents, the washing occurs over the whole surface of the froth rather than in a focused region of the froth.

In addition, U.S. Pat. No. 4,668,382 (the contents of the entirety of which are incorporated herein by this reference) changes the configuration from a tank with vertical walls to converging walls so that the froth is squeezed (crowded) as it collects on the liquid surface. This allows for a higher froth depth than would normally occur, thus permitting better collection selectivity in the portion of froth overflowing into the collection launder. This design however requires an expensive fabrication process to make the converging sides.

U.S. Pat. No. 6,832,690 (the contents of the entirety of which are incorporated herein by this reference) also describes a method of squeezing the froth in a complex geometry, while U.S. Pat. No. 5,251,764 (the contents of the entirety of which are incorporated herein by this reference) describes a complex hydraulically-operated system. Froth zone surface fouling can be troublesome in these modifications of the original Jameson cell design.

In column flotation cells such as the MICROCEL™, U.S. Pat. Nos. 4,981,582 and 5,167,798; the Deister Column Cell, U.S. Pat. No. 5,078,921; and the Multistage Loop-Flow Flotation (MSTLFLO) column, U.S. Pat. No. 5,897,772 (the contents of the entirety of each of which are incorporated herein by this reference), the collection, separation, and froth zones and froth washing are combined in a tall, cylindrical tank, which is less effective and more expensive to construct. In these column flotation cells, the froth at the top of the column overflows into an outer launder that surrounds the column. Sometimes an additional central launder is added to increase the froth discharge area when it is necessary to achieve rapid removal of voluminous froth.

Mechanical flotation cells typically employ a rotor and stator mechanism for gas induction, bubble generation, and liquid circulation thus providing for bubble and particle collision. The ratio of vessel height to diameter, termed the "aspect ratio", usually varies from about 0.7 to 2. Typically, four or more cells each having a centrally mounted rotor and stator mechanism are arranged in series. The liquid-particle dispersion is fed into the cell and air is sucked into the cell through a hollow shaft agitator. The air stream is broken by the rotating impeller, so that small bubbles are emitted from the end of the impeller blades. An auxiliary blower may also be used to provide sufficient gas flow to the cell. Rising bubbles together with attached particles form a froth layer on the top of the liquid surface. The froth layer overflows or is skimmed off mechanically from the top. Non-floated components are withdrawn from the bottom of the cell. Mechanical flotation cells are often used in mineral processing systems; however they have the disadvantage of large space requirements, long liquid residence times, and high power consumption.

For example, U.S. Pat. Nos. 4,425,232 and 4,800,017 (the contents of the entirety of which are incorporated herein by this reference) describe mechanical flotation separation utilizing a flotation cell provided with a rotor-stator assembly submerged in a slurry and in which rotor blades agitate the slurry thoroughly mixing the solids and liquid and introducing air to the mixture for aeration and generation of froth on the liquid surface. Particles of minerals attach to carrier air bubbles which are naturally buoyant and form the froth, this being the effective mechanism for mineral recovery. The floating froth is removed from the top of the slurry together with the attached mineral particles which are recovered as froth is collapsed and dewatered.

In all of these previously described processes, the desired particles that have prematurely disengaged (i.e., desorbed or detached) from the bubbles are inefficiently contacted with rising gas bubbles over the entire cross sectional area of the tank, thus lowering the chance of recapturing them. In addition, these designs typically have froth collection launders around the perimeter, which reduces the froth density as the froth spreads from the center outward (from low surface area to high surface area) thereby reducing the froth height and the selectivity of froth overflow.

SUMMARY OF THE INVENTION

Described is a highly efficient process and apparatus (flotation cell) for increasing the collection effectiveness of bubbles and improving the purity of the froth produced in an adsorptive bubble separation process, in which collected hydrophobic materials (particles) are attached to the bubbles. These materials typically include solids, liquids, or both. Above the froth-liquid interface within the flotation cell is the froth zone wherein the bubble-particle agglomerates form a floating froth layer. By the design disclosed herein, this froth naturally floats toward an open central froth collection launder into which it overflows. The action of the rising bubbles at the perimeter pushing the froth layer toward the reduced surface area of the center squeezes (crowds) the froth causing bubble coalescence and increased liquid drainage thereby achieving an increased concentration of collected materials.

The improved adsorptive bubble separation design may be utilized in any flotation cell by forcing floating froth to flow on the liquid surface to a region of lower surface area before overflowing into a collection launder. This improved froth collection design may be utilized in the operation of mechanical flotation cells, pneumatic flotation cells such as the Jameson cell, Multistage Loop-Flow flotation columns, and bubble flotation columns (also known as "Canadian Columns") by replacement of the their perimeter collection launder with a central collection launder.

As a consequence of the design, the length of the collection launder lip (referring to the launder edge which the froth overflows) is shorter than the length of the perimeter of the separation apparatus. This is in contrast to processes of the prior art wherein the collection launder is located around the perimeter of the apparatus so that the launder lip length is the same length as the perimeter. In those prior art designs where a central launder is also used, the launder lip length is further increased. The design of the invention is especially useful in the recovery or removal of low concentrations of hydrophobic materials in water. In oil recovery from water, for example, it is desirable to concentrate the oil in the froth to the greatest extent possible before it is removed from the flotation cell. This design is also useful for the dewatering of microalgae in very dilute microalgal cultures.

In any adsorptive bubble separation process, a portion of the desired hydrophobic material is not captured by, or is dislodged from, the rising bubbles. An optional performance enhancement in the instant design provides a means for forcing re-contact of these disengaged particles with rising bubbles at the perimeter. This enhancement is achieved by the use of a baffle in the separation vessel which causes the disengaged particles to flow down and outward with the liquid draining from the froth to re-contact the rising bubbles at the perimeter. This re-contact with bubbles encourages re-adsorption of the desired hydrophobic material resulting in better recovery than generally obtained in the prior art.

The process for adsorptive bubble separation can be repeated one or more times in order to affect an efficient countercurrent flow of froth and draining liquid for highly efficient particle capture. The process for adsorptive bubble separation can be operated batchwise or continuously. Continuous operation is preferred in most applications.

DETAILED DESCRIPTION OF THE INVENTION

Figure 1:
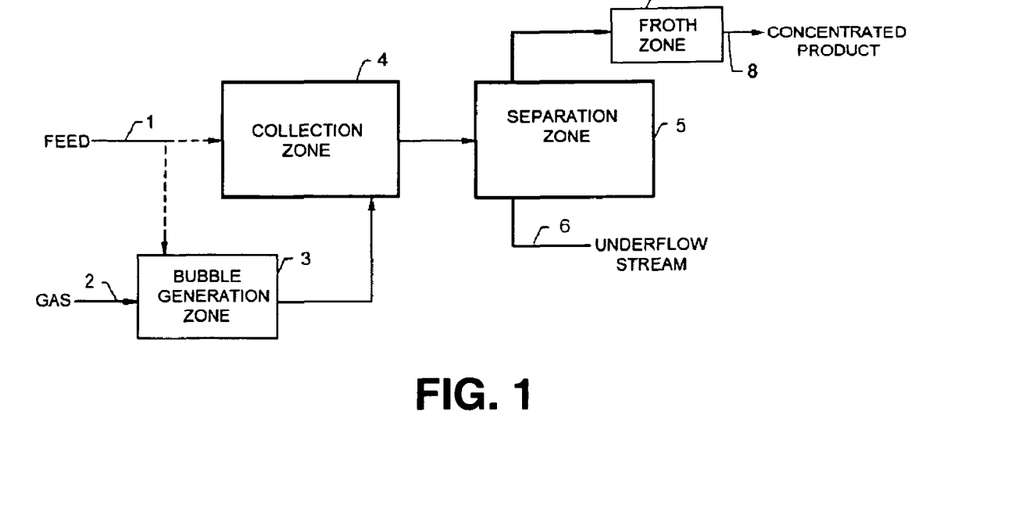
FIG. 1 is schematic block diagram of the process.

As shown in FIG. 1, the froth flotation device includes a bubble generation zone 3, a collection zone 4, a separation zone 5, and a froth zone 7. Some or all of these zones may or may not occupy the same vessel. The liquid-particle dispersion feed 1 enters the froth flotation device at either the collection zone 4 or the bubble generation zone 3 or both, depending on the equipment chosen. In either event, a gas 2 is dispersed through the bubble generation zone 3 and/or the collection zone 4 to produce a gas-liquid-particle dispersion. It is desirable to produce a large number of small bubbles to maximize the surface area of gas available for collision with hydrophobic particles in a given volume of the feed dispersion 1.

In the collection zone 4, the hydrophobic particles are mixed with the fine bubbles under conditions that promote intimate contact to produce the gas-liquid-particle dispersion. The bubbles collide with the hydrophobic particles and form bubble-particle agglomerates. It is desirable to generate intense mixing in the collection zone 4 to cause a high frequency of collisions in order to achieve high particle capture efficiency.

After the bubble-particle agglomerates are formed in the collection zone 4, they are then separated from the particle-depleted liquid in the separation zone 5, typically by gravity. The density of the gas is generally at least two to three orders of magnitude less than that of the liquid. The density difference promotes floating of the bubble-particle agglomerates to the surface of the liquid, where the agglomerates accumulate as a froth in the froth zone 7.

The froth, enriched in hydrophobic particles, overflows the froth zone 7 as stream 8. The underflow stream (tails) 6, which is the liquid depleted in hydrophobic particles, exits the froth flotation device and may be treated again in a secondary flotation cell, recycled or discarded.

Figure 2:
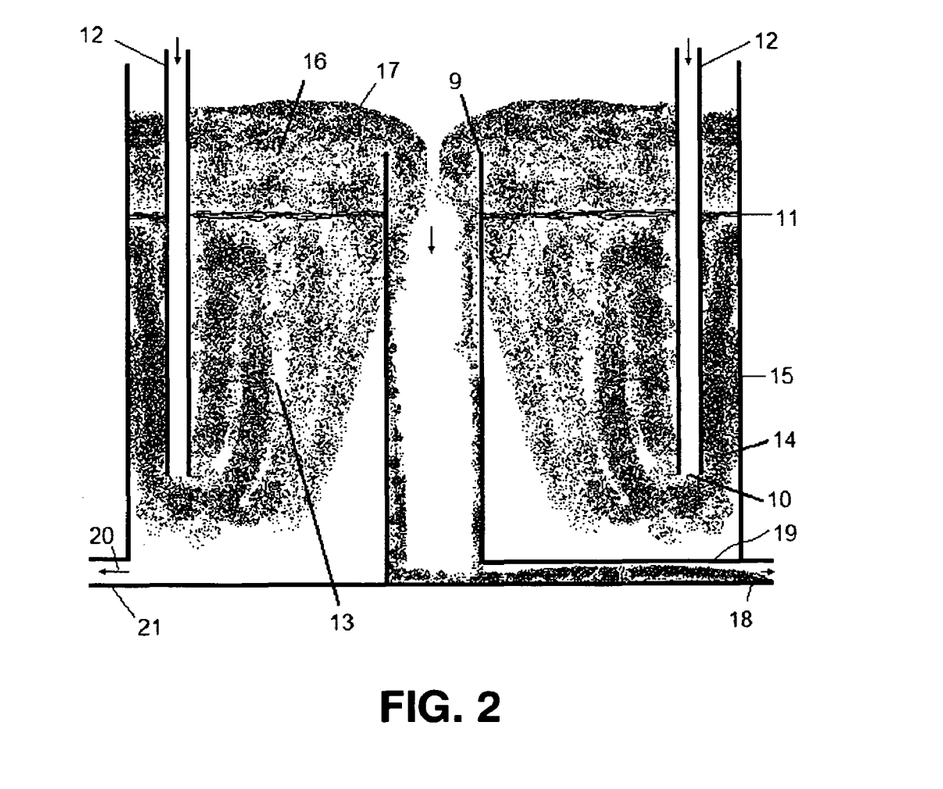
FIG. 2 is a sectional view of a cylindrical separation apparatus in which the gas-liquid-particle dispersion introduction ducts are arranged near the perimeter of the vessel and the froth collection launder is in the center.

FIG. 2 shows an apparatus for adsorptive bubble separation in which the gas-liquid-particle dispersion 10 is introduced below the liquid surface (froth-liquid interface) 11 through introduction ducts 12 into the separation zone 13. In all embodiments of this invention the gas may comprise air, nitrogen, argon, helium, carbon dioxide, gas from the combustion of carbonaceous material, solvent vapor, carbon dioxide from a gasification plant, or combinations thereof. The gas may also be pre-saturated with liquids, especially liquids that are contained in the feed dispersion. The gas-liquid-particle dispersion 10 can be produced by methods known in the prior art such as aspiration of the gas into the liquid-particle dispersion using an eductor, a plunging jet, or an agitated system.

The introduction ducts 12 introducing the gas-liquid-particle dispersion 10 may be vertical, have a vertical section, or be essentially vertical so that it contains the column of foam in a manner so that sufficient vacuum is maintained in the top of the duct to maintain a column of at least some of the gas-liquid-particle dispersion in the duct. Alternatively (or additionally), the introduction ducts may enter the flotation cell through the side of the vessel. This embodiment may also have two or more introduction ducts 12 evenly spaced near the perimeter of the vessel. It is preferred to have four or more introduction ducts 12 evenly spaced near the perimeter of the vessel.

The gas-liquid-particle dispersion 10 exiting from the introduction ducts 12 has been created such that the liquid-particle dispersion feed has been brought into intimate contact with the gas with enough energy and for sufficient time that an acceptable percentage of the hydrophobic material has been collected on the bubbles. The introduction ducts 12 may be cylindrical in shape, but other geometries could be used, including but not limited to rectangles, squares, ovals, triangles, and other polygons. The introduction ducts 12 may be constructed from any material used in the art, including but not limited to polyvinyl chloride (PVC), high-density polyethylene (HDPE), polycarbonate, other polymers, glass, fiberglass, steel, iron, other metals, concrete, tile, or other construction materials.

The bottoms of the introduction ducts 12 are submerged below the surface of the liquid 11 within the separation zone 13 where the exiting gas-liquid-particle dispersion 10 begins to coalesce into larger bubbles 14 and rise toward the liquid surface 11 carrying the collected materials. The separation zone 13 can be configured in any shape so long as the residence time is sufficiently great to allow for bubble coalescence and the separation of the bubble-particle agglomerates and liquid stream. Even though the separation zone 13 may be cylindrical, square, rectangular, hexagonal, or other shape, it is preferable to use a cylindrical design. The outer wall 15 of the flotation cell may be constructed from any material used in the art, including but not limited to polyvinyl chloride (PVC), high-density polyethylene (HDPE), polycarbonate, other polymers, glass, fiberglass, steel, iron, other metals, concrete, tile, earth, stone, or other construction materials.

The rising bubble-particle agglomerates 14 accumulate as a froth 17 above the liquid surface (froth-liquid interface) 11 in the froth zone 16. In this zone, the froth continues to drain, purifying the froth and concentrating the collected material. As additional bubbles rise forming more froth, they push the accumulated froth on the surface toward the center where the upper portion overflows the launder lip into the froth collection launder 9. This movement toward the reduced surface area of the center squeezes the froth helping to cleanse and drain it. Wash water may be added to the froth from above if desired to further purify it. Any suitable liquid can be used for the froth washing operation. Suitable liquids include, but are not limited to water, liquids that are native to the feed dispersion, solutions of surface treatment and conditioning agents, and combinations thereof.

The purified froth 17 overflows into a central collection launder 9 that extends above the liquid surface level 11. The collection launder 9 can be of any shape, but it is preferably the same geometric shape as the flotation cell. The central collection launder 9 is most preferably a circular pipe or hollow column. The collection launder 9 may be constructed from any material used in the art, including but not limited to polyvinyl chloride (PVC), high-density polyethylene (HDPE), polycarbonate, other polymers, glass, fiberglass, steel, iron, other metals, concrete, tile, or other construction materials. The froth and collapsed froth 18 drains down the collection launder 9 and then exits the flotation cell through the bottom or the side via a drain line 19.

The feed liquid depleted in hydrophobic particles (tails) 20 underflows the flotation device through a bottom or side tails line 21 and may be treated again in a secondary flotation cell, recycled or discarded. The bottom of the flotation cell may be flat, hemispherical or conical. In processes in which solids settle to the bottom, a sloped-flat, hemispherical or conical bottom with bottom tails line 21 is desired for improved solids removal. The liquid level 11 within the flotation cell may be controlled by controlling the liquid flow through the tails line 21. Optionally, liquid level control may be conveniently maintained without valves or control devices by the use of one or more overflow side arms or swing arms.

Figure 3:
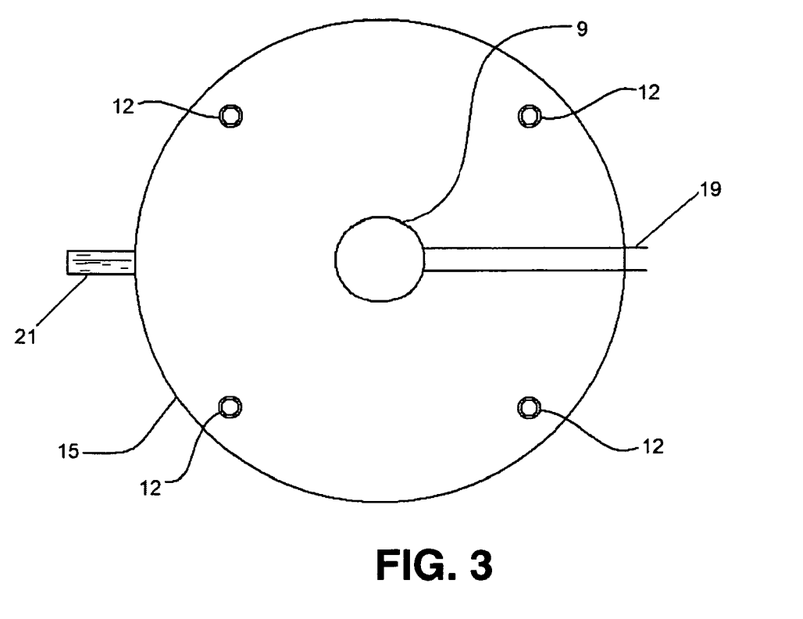
FIG. 3 is a top view of the apparatus of FIG. 2.

FIG. 3 shows a top view of the apparatus for adsorptive bubble separation of FIG. 2 employing four introduction ducts 12.

Figure 4:
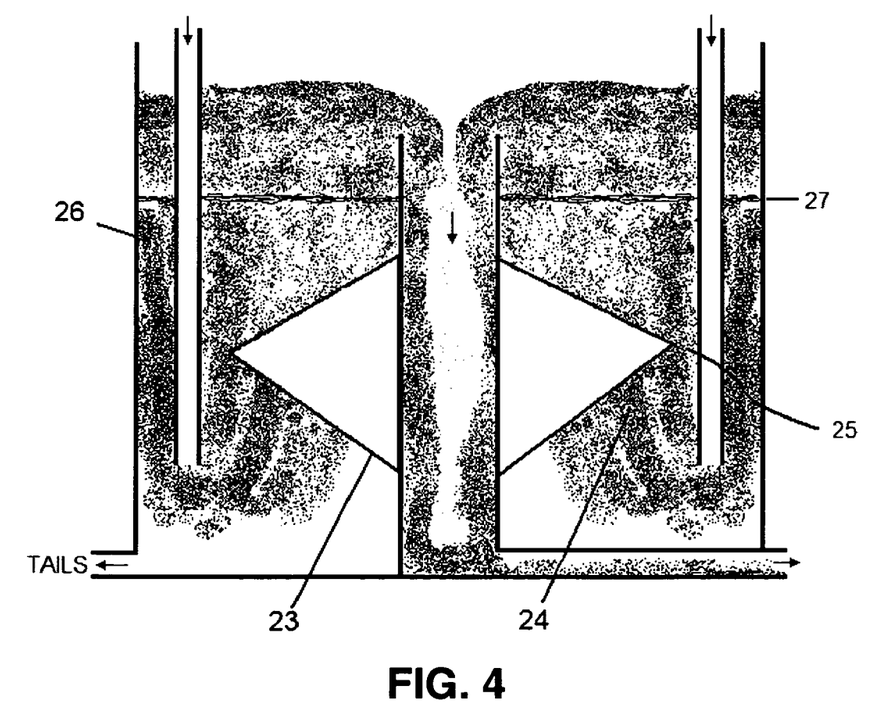
FIG. 4 is a sectional view of a cylindrical separation apparatus in which the gas-liquid-particle dispersion introduction ducts are arranged near the perimeter of the vessel, the froth collection launder is in the center and a baffle is used to direct disengaged particles back to the perimeter for re-contact with rising bubbles.

FIG. 4 shows an optional performance enhancement to the apparatus for adsorptive bubble separation of FIGS. 2 and 3. This optional enhancement includes a baffle 23 to direct the disengaged particles to flow down and outward with the liquid draining from the froth to re-contact the rising bubbles at the perimeter. This re-contact with bubbles encourages re-adsorption of the desired hydrophobic material resulting in better recovery than would be obtained by methods in the prior art.

A froth baffle 23 directs the bubbles 24 outward to the gap 25 between the baffle 23 and the perimeter wall 26 where they then rise toward the liquid surface 27. Likewise disengaged particles that are sinking are directed outward by baffle 23 to the gap 25 where they will be re-contacted with rising bubbles. The froth baffle 23 may be of any shape which directs the rising bubbles and the sinking particles to a location near the perimeter. The baffle 23 may be conical, flat, tapered, or sloped and constructed from any material used in the art, including but not limited to PVC, HDPE, polycarbonate, rubber, other polymers, glass, fiberglass, steel, iron, other metals, concrete, tile, or other construction materials.

Figure 5:
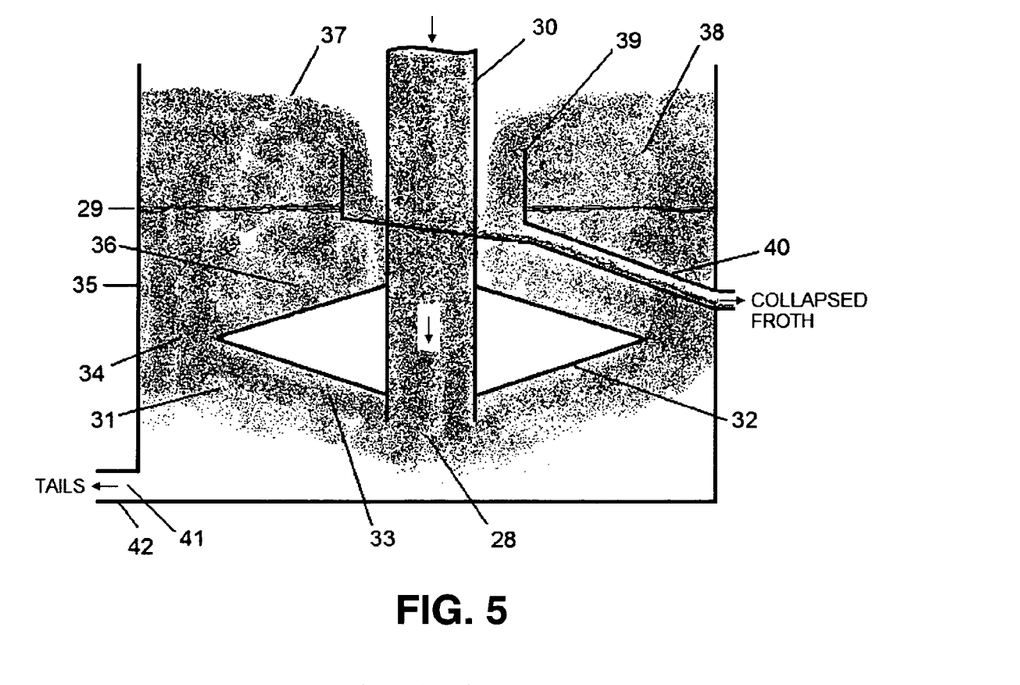
FIG. 5 is a sectional view of a cylindrical separation apparatus in which a single gas-liquid-particle dispersion introduction duct is located in the center and the central froth collection launder is attached to the duct in an annular fashion, a baffle is used to direct the rising bubbles to the perimeter.

FIG. 5 shows an apparatus for adsorptive bubble separation in which the gas-liquid-particle dispersion 28 is introduced below the liquid surface 29 through one central introduction duct 30 into the separation zone 31. A froth baffle 32 directs the bubbles 33 outward to the gap 34 between the baffle 32 and the perimeter wall 35 where they then rise toward the liquid surface 29. Likewise disengaged particles 36 that are sinking are directed outward by baffle 32 to the gap 34 where they will be re-contacted with rising bubbles. The froth baffle 32 may be of any shape which directs the rising bubbles and the sinking particles to a location near the perimeter. The baffle may be conical, flat, tapered, or sloped and constructed from any material used in the art, including but not limited to PVC, HDPE, polycarbonate, rubber, other polymers, glass, fiberglass, steel, iron, other metals, concrete, tile, or other construction materials.

The rising bubble-particle agglomerates accumulate, as a froth 37, above the liquid surface 29 in the froth zone 38. In this zone, the froth continues to drain, purifying the froth and concentrating the collected material. As additional bubbles rise forming more froth, they push the accumulated froth on the surface toward the center where the upper portion overflows the launder lip into the collection launder 39. This movement toward the reduced surface area of the center squeezes the froth helping to cleanse and drain it. Wash water may be added to the froth from above if desired to further purify it.

The purified froth 37 overflows into a central collection launder 39 which extends above the liquid surface level 29. The collection launder 39 can be of any shape, but it is preferred that the collection launder 39 be an annulus around a tubular introduction duct 30. The collection launder 39 may be constructed from any material used in the art, including but not limited to polyvinyl chloride (PVC), high-density polyethylene (HDPE), polycarbonate, other polymers, glass, fiberglass, steel, iron, other metals, concrete, tile, or other construction materials. The froth or collapsed froth 37 drains down the collection launder 39 and then exits the flotation cell through the bottom or the side via a drain line 40.

The feed liquid depleted in hydrophobic particles (tails) 41 underflows the flotation device through a bottom or side tails line 42 and may be treated again in a secondary flotation cell, recycled or discarded. The bottom of the flotation cell may be flat, hemispherical or conical. In processes in which solids settle to the bottom, a sloped-flat, hemispherical or conical bottom with bottom tails line 42 is desired for improved solids removal. The liquid level 29 within the flotation cell may be controlled by controlling the liquid flow through the tails line 42. Optionally, the liquid level 29 may be maintained by the use of one or more self-leveling devices such as an overflow side arm or swing arm.

One of the design parameters in flotation cell design is Jg (the superficial gas rise rate), and it is typically calculated by dividing the gas flow rate entering the cell by the cell area. High Jg rates (greater than 1 cm per second) will typically produce high recovery as a rapid bubble rise rate leaves less time for the bubbles to coalesce and particles to disengage. In this rising stream, gangue and liquid can be entrained in the flow also. Lower Jg rates (less than 1 centimeter per second) allow more time for bubble coalescence and drainage of the froth to produce a more pure froth. An even rise of bubbles is assumed in the calculation of Jg. In the prior art, it is understood that uniformity in the froth flow path results in uniform treatment of the froth and gives more predictable performance. With a central froth baffle in a cylindrical tank, froth distribution takes place in a radial direction with constant distances and a uniform inward froth flow path throughout 360 degrees.

Figure 6:
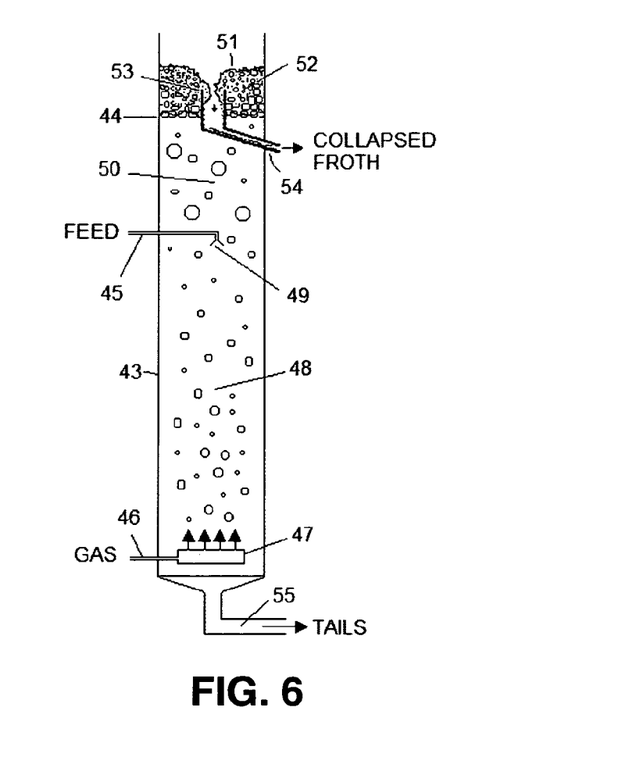
FIG. 6 is an illustration of how a conventional bubble column can be modified with a central froth launder to utilize the design of the invention.

FIG. 6 shows a flotation column embodiment of the invention in which the collection, separation, and froth zones and optional froth washing are combined in a tall, cylindrical tank 43. This design is an improvement of the conventional bubble column which is also known as the "Canadian Column". The cross section may be circular, square or hexagonal. The liquid-particle dispersion enters the column at a point below the liquid surface (froth-liquid interface) 44 through line 45. The gas enters the base of the column through line 46 and is dispersed into fine bubbles, typically by means of a sparger 47 or it is introduced as an aerated liquid.

The countercurrent flow of gas and feed dispersion results in bubble and particle collision in the collection zone 48 which is defined as the region below the feed distributor 49. The separation zone 50 for the column is above the feed distributor 49 and below the froth-liquid interface 44.

The rising bubble-particle agglomerates accumulate as a froth 51 above the liquid surface 44 in the froth zone 52. In this zone the froth continues to drain, purifying the froth and concentrating the collected material. As additional bubbles rise forming more froth, they push the accumulated froth on the surface toward the reduced surface area of the center where the upper portion overflows the launder lip into the collection launder 53. This movement toward the center squeezes the froth helping to cleanse and drain it. Wash water may be added to the froth from above if desired to further purify it.

The purified froth 51 overflows into a central collection launder 53 which extends above the froth-liquid interface 44. The collection launder 53 can be of any shape, but it is preferably the same geometric shape as the flotation cell. The central collection launder 53 is most preferably a circular pipe or hollow column. The collection launder 53 may be constructed from any material used in the art, including but not limited to polyvinyl chloride (PVC), high-density polyethylene (HDPE), polycarbonate, other polymers, glass, fiberglass, steel, iron, other metals, concrete, tile, or other construction materials.

The froth or collapsed froth 51 drains down the collection launder 53 and then exits the flotation cell through the bottom or the side via a drain line 54. The tails, depleted of hydrophobic particles, underflows the column through a bottom or side tails line 55 and may be treated again in a secondary flotation cell, recycled or discarded. The bottom of the flotation cell may be flat, hemispherical or conical. In processes in which solids settle to the bottom, a sloped-flat, hemispherical or conical bottom with bottom tails line 55 is desired for improved solids removal. The liquid level 44 within the flotation cell may be controlled by controlling the liquid flow through the tails line 55. Optionally, the liquid level 44 may be maintained by the use of one or more self-leveling devices such as an overflow side arm or swing arm.

Figure 7:
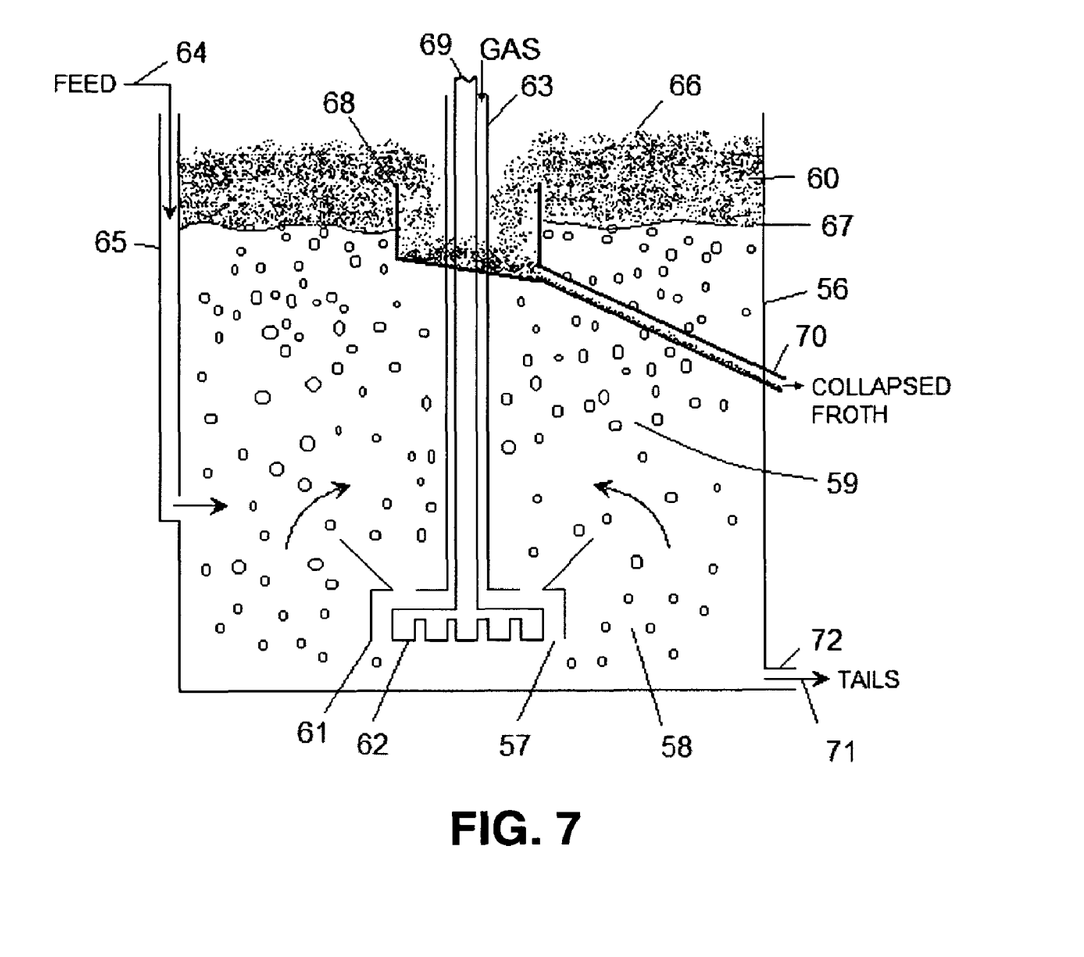
FIG. 7 is an illustration of how a mechanical flotation cell can be modified with a central froth launder to utilize the design of the invention.

FIG. 7, shows a mechanical flotation cell embodiment of the invention in which the bubble generation zone 57, collection zone 58, separation zone 59, and froth zone 60 are combined into a single large tank 56. Mechanical cells typically employ a rotor and stator mechanism 61 for gas induction, bubble generation, and liquid circulation providing for bubble and particle collision. Typically, four or more cells similar to that in FIG. 7, each having a centrally mounted rotor and stator mechanism 61, are arranged in series to improve efficiency. An auxiliary blower is occasionally installed to provide sufficient gas flow to the cell.

The gas is dispersed into fine bubbles by a rotating impeller 62, which serves as the bubble generator. The rotating impeller creates a low pressure zone that induces gas to flow through an aspiration tube 63 into the collection zone 58 where it is dispersed into fine bubbles and mixed with the liquid-particle dispersion as it circulates in the bottom of the cell.

The properly designed rotor and stator mechanism entrains the proper amount of gas, disperses it into fine bubbles, and mixes the gas with liquid to accomplish sufficient contact between the particles and the bubbles. Good mixing and sufficient liquid residence time are necessary in the two phase mixing region to provide high bubble and particle collision efficiency, and good flotation performance. Rotor and stator mechanisms include those produced by Don-Oliver Incorporated of Millford, Conn.; Denver Equipment Company which is a division of Svedala of Colorado Springs, Colo.; Wemco Products of Salt Lake City, Utah; and Outomec Oy of Espoo, Finland.

The liquid dispersion enters the mechanical cell as a feed stream 64 through a feed box 65. Bubble and particle contact results from turbulence generated by the rotating impeller 62. The bubbles with attached particles pass out of the collection zone 58 into the separation zone 59, which is relatively quiescent, where they float to the surface and separate from the liquid phase.

The rising bubbles accumulate as a froth 66 above the liquid surface (froth-liquid interface) 67 in the froth zone 60. In this zone the froth continues to drain, purifying the froth and concentrating the collected material. As additional bubbles rise forming more froth, they push the accumulated froth on the surface toward the reduced surface area of the center where the upper portion overflows the launder lip into the collection launder 68. This movement toward the center squeezes the froth helping to cleanse and drain it. Wash water may be added to the froth from above if desired to further purify it.

The purified froth 66 overflows into a central collection launder 68 that extends above the liquid surface level 67. The collection launder 68 can be of any shape, but it is preferred that the collection launder 68 be an annulus around a circular aspiration tube 63 and rotor shaft 69. The collection launder 68 may be constructed from any material used in the art, including but not limited to PVC, HDPE, polycarbonate, other polymers, glass, fiberglass, steel, iron, other metals, concrete, tile, or other construction materials. The froth or collapsed froth drains down the collection launder 68 and then exits the flotation cell through the bottom or the side via a drain line 70.

The liquid phase recirculates in the collection zone 58, but eventually exits the cell as an underflow stream 71 through a bottom or side tails line 72. The tails may be treated again in a secondary flotation cell, recycled or discarded. The bottom of the flotation cell may be flat, hemispherical or conical. In processes in which solids settle to the bottom, a sloped-flat, hemispherical or conical bottom with bottom tails line 72 is desired for improved solids removal. The liquid level 67 within the flotation cell may be controlled by controlling the liquid flow through the tails line 72. Optionally, the liquid level 67 may be maintained by the use of one or more self-leveling devices such as an overflow side arm or swing arm.

Figure 8:
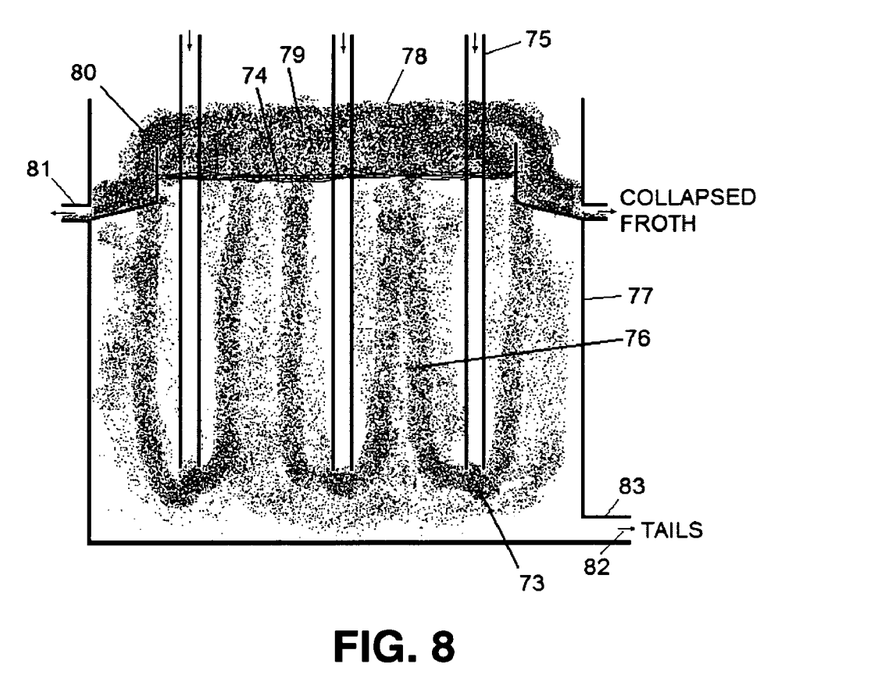
FIG. 8 is a sectional view illustrating a rectangular separation apparatus with gas-liquid-particle dispersion ducts arranged on the diagonal and froth collection launders in the opposite corners.

FIG. 8, shows an example of how our discovery for improving froth purity by causing the froth to squeeze into a region of lower surface area can be utilized in alternate flotation cell geometries. FIG. 8 shows a rectangular, or preferably square, flotation cell embodiment of the invention in which the gas-liquid-particle dispersion 73 is introduced below the liquid surface (froth-liquid interface) 74 through two or more introduction ducts 75 into the separation zone 76. It is preferred in this embodiment to have two or more introduction ducts 75 evenly spaced along a diagonal of the vessel. The introduction ducts 75 may be constructed from any material used in the art, including but not limited to polyvinyl chloride (PVC), high-density polyethylene (HDPE), polycarbonate, other polymers, glass, fiberglass, steel, iron, other metals, concrete, tile, or other construction materials.

The bottoms of the introduction ducts 75 are submerged below the surface of the liquid 74 within the separation zone 76 where the exiting gas-liquid-particle dispersion 73 begins to coalesce into larger bubbles and rise carrying the collected materials. The separation zone 76 in this embodiment is square or rectangular and of such height as to allow for bubble coalescence and the separation of froth and liquid streams. The outer wall 77 of the flotation cell may be constructed from any material used in the art, including but not limited to PVC, HDPE, polycarbonate, other polymers, glass, fiberglass, steel, iron, other metals, concrete, tile, earth, stone, or other construction materials.

The rising bubble-particle agglomerates accumulate as a froth 78 above the liquid surface (froth-liquid interface) 74 in the froth zone 79. In this zone the froth continues to drain, purifying the froth and concentrating the collected material. As additional bubbles rise forming more froth, they push the accumulated froth on the surface toward the two corners where the upper portion overflows the launder lips into the collection launders 80. This movement toward the lower-surface-area corners squeezes the froth helping to cleanse and drain it. Wash water may be added to the froth from above if desired to further purify it.

The purified froth 78 overflows into the corner collection launders 80 which extend above the liquid surface level 74. The collection launders 80 may be any shape although shapes that fit tightly in the corner are preferred. These shapes would include square, rectangular, triangular, quarter-circle and circular. The collection launders 80 may be constructed from any material used in the art, including but not limited to PVC, HDPE, polycarbonate, other polymers, glass, fiberglass, steel, iron, other metals, concrete, tile, or other construction materials. The froth or collapsed froth 78 drains down the collection launders 80 and then exits the flotation cell through the bottom or the side via drain lines 81. Alternatively, the collection launders in this rectangular embodiment may also be exterior to the flotation cell by the use of a corner notch which serves as the froth collection launder lip.

The feed liquid depleted in hydrophobic particles (tails) 82 underflows the flotation device through a bottom or side tails line 83 and may be treated again in a secondary flotation cell, recycled or discarded. The bottom of the flotation cell may be flat, hemispherical or conical. In processes in which solids settle to the bottom, a sloped-flat, hemispherical or conical bottom with bottom tails line 83 is desired for improved solids removal. The liquid level 74 within the flotation cell may be controlled by controlling the liquid flow through the tails line 83. Optionally, liquid level control may be conveniently maintained without valves or control devices by the use of one or more overflow side arms or swing arms.

Figure 9:
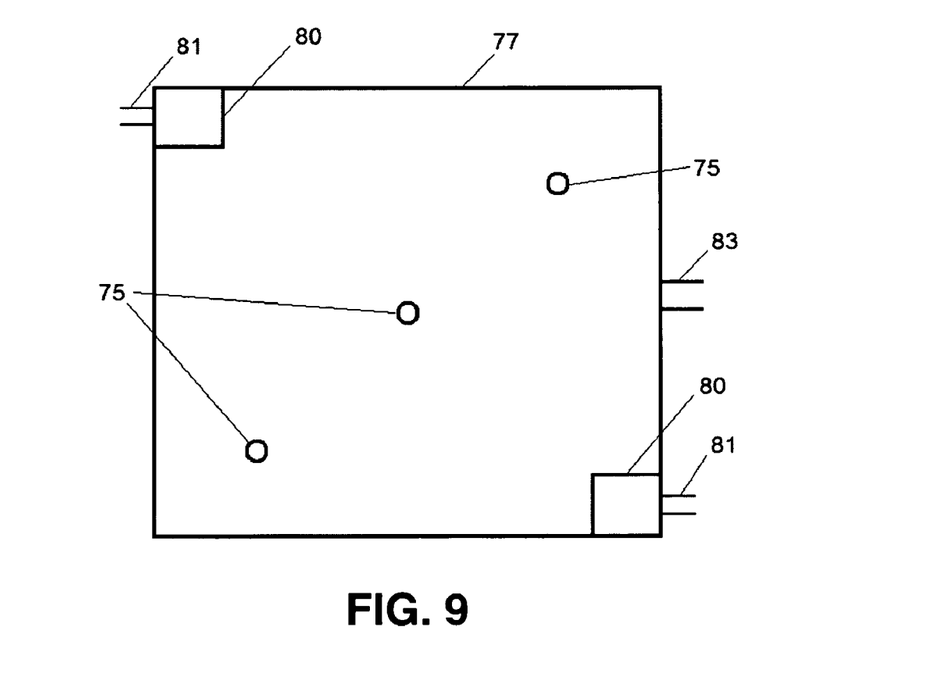
FIG. 9 is a top view of the rectangular apparatus of FIG. 8.

FIG. 9 shows a top view of the flotation cell embodiment of FIG. 8 employing three introduction ducts 75.

In the process of the invention the feed dispersion comprises particles and a carrier fluid, usually water. The particles may comprise solid particles or liquid droplets, or combinations thereof. Examples of the solid particles include, but are not limited to minerals, gangue, micro-organisms, coal, inks, pigments, or combinations thereof. Examples of liquid droplets include, but are not limited to organic solvents, metal extraction solvents, dyes, inks, oils, hydrocarbons, fuels, triglycerides, carotenoids, natural products, biodiesel, or other fluids that are above their melting point and below their boiling point at the system pressure and temperature. Practical examples of the feed dispersions requiring separation include but are not limited to minerals and gangue, aqueous dispersions of micro-organisms (microalgae, bacteria, fungi, and/or viruses), aqueous dispersions of oil droplets and unwanted particulates, aqueous dispersions of triglycerides, coal and unwanted materials (e.g., ash), particles in waste-water treatment streams, and inks and/or adhesives on paper for recycling, or combinations thereof. Micro-organisms in the feed may be alive or dead, whole or ruptured. The apparatus and process of this invention is especially useful for the concentration (dewatering) of ruptured microalgal cells and microalgal cellular components in water. Additives may be introduced to facilitate flotation of micro-organism cells such as alum, ferric chloride, poly-electrolytes, polymers, and other flocculants known in the art. The carrying liquid may be water, brine, seawater, aqueous solutions, growing media for the microalgae or reagents or a combination of any of these.

In biochemical process engineering, adsorptive bubble separation finds utility in isolation or concentration of valuable natural products such as are produced by, for example, microalgae. Often in such applications the desired organism or biochemical product is present in very low concentration. In such cases it is necessary therefore to feed large volumes of a very dilute aqueous dispersion of the desired material. See for example, "Harvesting of Algae by Froth Flotation," G. V. Levin, et al., Applied and Environmental Microbiology, volume 10, pages 169-175 (1962). U.S. Pat. Nos. 5,776,349 and 5,951,875, the contents of which are incorporated herein by this reference, disclose the use of a Jameson cell for dewatering an aqueous dispersion of ruptured microalgae cells.

The microalgae can be any species of microalgae one desires to separate from the carrying liquid. These species include, but are not limited to *Anabaena, Ankistrodesmus falcatus, Arthrospira (Spirulina) obliquus, Arthrospira (Spirulina) platensis, Botryococcus braunii, Chaetoceros gracilis, Chlamydomonas reinhardtii, Chlorella vulgaris, Chlorella pyrenoidosa, Chlorococcum littorale, Cyclotella cryptica, Dunaliella bardawil, Dunaliella salina, Dunaliella tertiolecta, Dunaliella viridis, Euglena gracilis, Haematococcus pluvialis, Isochrysis galbana, Nannochloris, Nannochloropsis salina, Navicula saprophila, Neochloris oleoabundans, Nitzschia laevis, Nitzschia alba, Nitzschia communis, Nitzschia paleacea, Nitzschia closterium, Nostoc commune, Nostoc flagellaforme, Pleurochrysis carterae, Porphyridium cruentum, Prymnesium, Pseudochoricystis ellipsoidea, Scenedesmus obliquus, Scenedesmus quadricauda, Scenedesmus acutus, Scenedesmus dimorphus, Skeletonema costatum, Spirogyra, Spirulina, Synechoccus, Amphora, Fragilaria, Schizochytrium, Rhodomonas*, and genetically-engineered varieties of these microalgal species. It should be understood that an additional reason for the separation of microalgae may be to clean the carrying liquid, rather than just for the purpose of concentrating microalgal biomass.

In mineral processing applications, the feed dispersion is conditioned using surface chemistry treatments as are known in the art that render the desired mineral hydrophobic. When the feed dispersion is contacted with gas, the hydrophobic materials attach and rise with the bubbles. The undesired gangue material then flows downward with the liquid. This invention is also useful in those instances where the undesired material is rendered hydrophobic and is removed with the froth. In such cases the underflow contains the desired material.

Due to the difficulty in transporting froths in ducts and pipes, it is critical to collapse the purified froth in the collection launder. The purified froth which overflows into the collection launder naturally collapses or is treated in one of several ways known in the art to collapse the froth and isolate the concentrated material. With more persistent froths, more aggressive action must be taken to collapse them. The use of froth sprays in the froth collection launder is common in the prior art. The liquid used for the sprays can be water or any other liquid. So as to not dilute the collected material, the liquid portion of the collapsed froth can be recirculated through the spray nozzles. It is important that the spray nozzles be of a design to prevent clogging. Air or gas selected from those used for creation of the foam can also be used to break the froth.

Persistent froths (which do not collapse easily) are typically broken down by the use of sprays of liquid into the collection launders after the froth has overflowed into them. When the froth is allowed to flow to the perimeter of the separation vessel for collection in launders, the area needing treatment is the entire perimeter of the vessel. This addition of spray liquid can be large thus diluting the froth and partially defeating the purpose of the operation. This dilution is undesirable because adsorptive bubble separation is commonly used for the concentration of a hydrophobic material. Therefore, the instant invention provides an improvement in that the central collection launder has a lower surface area and requires less spray volume.

Chemical methods for breaking froth are also known in the prior art and include, but are not limited to the use of chemical defoamers. These defoamer liquids can be sprayed on the froth surface or distributed within a wetted pad that contacts the froth as it flows into the froth collection launder. These chemical methods are also applicable for use in the instant invention and the lower surface area of the central collection launder may result in the use of less chemical defoamer.

Mechanical methods to break the froth include, but are not limited to sonication methods, vibrating or spinning objects in the froth region, etc. Also, combinations of chemical and mechanical coalescing techniques can be used to coalesce the bubbles and form a region enriched in the particles to be separated from the liquid stream. These mechanical methods are also applicable to use in the instant invention and the lower surface area of the central collection launder may use smaller and less expensive equipment.

Described are improved froth flotation separation processes that use partial vacuum (i.e., suction or downdraft) to pull the froth and/or collapsed froth into and through the froth collection launder and froth drain line. This improvement greatly assists froth collection (especially with persistent froths) because froth can be pulled by suction through the collection system more easily than it can be drained by gravity or pushed. This partial vacuum or suction can be generated by any method known in the art, but it is particularly useful if it is created as a result of the need to supply gas to generate the gas-liquid-particle dispersion. By supplying the gas for the gas-liquid-particle production from the head space of a tank receiving the collected froth and collapsed froth, the partial vacuum or suction is created. This vacuum-aided froth collection embodiment is illustrated in FIG. 10 in integration with the apparatus previously described in FIG. 2 but it may be used in any flotation cell using a froth collection launder.

The vacuum source for this optional performance enhancement may be generated by the gas blower or compressor 84 which provides the flotation gas 85 either for sparging into the flotation cell or for mixing with the liquid-particle dispersion 86 to give the gas-liquid-particle dispersion 87. This may be achieved by the use of a collapsed froth trap 88 from which the gas blower or compressor 84 obtains its supply of gas 89 via supply line 90. Alternatively the vacuum can be self-generated by the use of an aspirating aerator (e.g., aspirator, venturi or eductor) 91 which is used to create the gas-liquid-particle dispersion 87. In the case of self aspirating aerators, no gas blower or compressor 84 is needed but the vacuum is provided by the Venturi effect of the aspirating aerator 91. Other benefits of this vacuum-aided froth collection embodiment are the pre-saturation of the flotation gas with the liquid in use and the ability to use a closed flotation cell with an inert gas.

Figure 10:
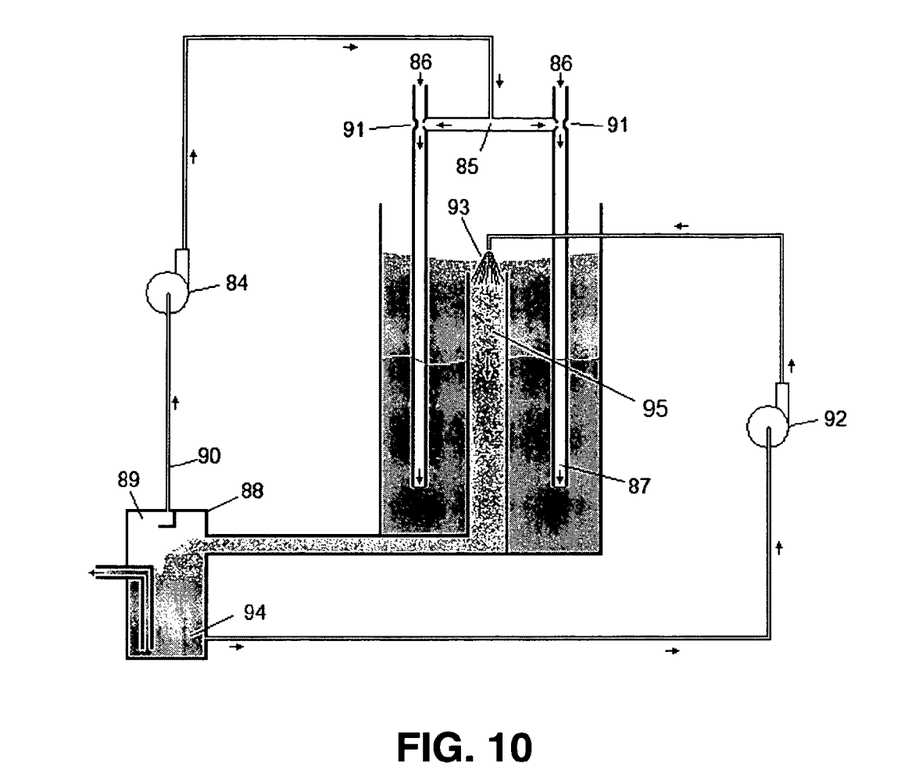
FIG. 10 is a sectional view illustrating an optional vacuum-aided froth collection system and an optional spray-aided froth collection system.

A second optional enhancement, spray-aided froth collection, illustrated in FIG. 10, may be used with or without the previous vacuum-aided froth collection. In this optional enhancement, a spray is used to improve froth collection. Pump 92 is used to generate the spray 93 from collapsed froth liquids 94 in trap 88. The spray 93 drives the persistent froth into the froth collection launder 95. The use of collapsed froth liquids for this spray prevents dilution of the collected materials.

In the case of particulate flotation, where the gangue material is denser than the liquid in the feed dispersion, a sloped bottom and a solids relief discharge will be needed to remove solids from the separation vessel. If the feed rate of the feed dispersion is somewhat constant, this solids relief discharge can be controlled by the use of a small valve set to discharge from the sloped bottom and remove the solids in a heavy slurry. In another aspect, this removal could be through a small solids handling pump.

Any suitable liquid can be used for the optional froth washing operation. Suitable liquids include, but are not limited to water, liquids that are native to the feed dispersion, solutions of surface treatment and conditioning agents, and combinations thereof.

Figure 11:
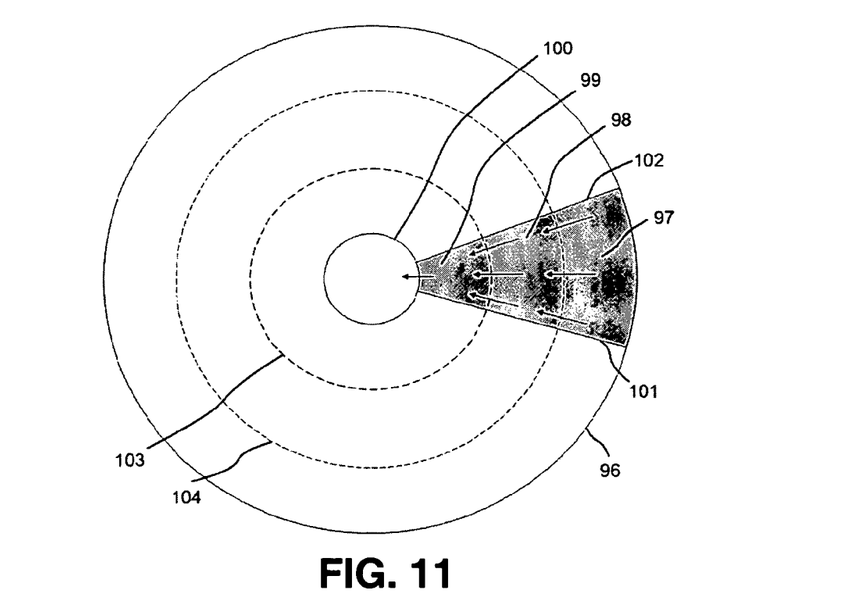
FIG. 11 is a top view of a cylindrical flotation cell of the type shown in FIGS. 2 and 3 which illustrates how the floating froth crowds into areas of lower surface area before spilling into the central froth collection launder.

FIG. 11 illustrates the froth crowding effect that occurs as the floating froth travels from a liquid surface region where it forms to a liquid surface region of lower area before spilling into the collection launder. This top view of a cylindrical flotation cell 96 of the type shown in FIGS. 2 and 3 emphasizes how the froth in, for example, region 97 must crowd into region 98 then region 99 before spilling into the central froth collection launder 100. Imaginary radial lines 101 and 102 and equi-distant concentric circles 103 and 104 are shown for illustration purposes only.

The process and apparatus for adsorptive bubble separation is further illustrated by the following Examples.

EXAMPLES

Example 1

Extractant Recovery from Copper Extraction Raffinate

A pilot-scale flotation cell is constructed with the design shown in FIG. 5 with the overall dimensions of the cylindrical separation zone section being 0.3 meters diameter and 1.3 meters in height. The annular clearance between the froth baffle and the outside is 1.25 centimeters and the froth collection launder lip diameter is 11.5 centimeters. The separation zone is fed through a 5 centimeter diameter introduction duct with an aqueous feed dispersion containing 0.02 wt % kerosene (solvent) with 0.005 wt % of Cyanex extractant. The feed dispersion rate is 35 liters per minute and the gas (air) flow rate is 8 liters per minute. The Jg in the separation zone is 0.62 centimeters/second, and this shows a moderate transport rate of collected material from the separation zone into the froth zone. The bubble-particle agglomerates residence time in the separation zone is 168 seconds, while the froth residence time in the froth zone is 562 seconds. Ninety percent of the kerosene fed to the flotation cell is recovered in the froth.

Example 2

Extractant Recovery from Copper Extraction Raffinate

A pilot-scale flotation cell is constructed with the design shown in FIG. 5 with the overall dimensions of the cylindrical separation zone being 0.3 meters diameter and 1.3 meters in height. The annular clearance between the froth baffle and the outside is 1.25 centimeters and the froth collection launder lip diameter is 8.9 centimeters. The separation zone is fed through a 7.5 centimeter diameter duct with an aqueous feed dispersion containing 0.02 wt % kerosene with 0.005 wt % Cyanex extractant. The feed rate is 53 liters per minute and the gas (air) flow rate is 13 liters per minute. The Jg in the separation zone is 1 centimeter/second, and this shows a high transport rate of collected material from the separation zone into the froth zone. The bubble-particle agglomerates residence time in the separation zone is 96 seconds, while the froth residence time in the froth zone is 321 seconds. Eighty-five percent of the kerosene fed to the flotation cell is recovered in the froth.

Example 3

Dewatering of an Algal Dispersion

A commercial-size flotation cell is constructed with the design shown in FIG. 5 with the overall dimensions of the cylindrical separation zone being 1.25 meters diameter and 2.5 meters in height. The annular clearance between the lower froth baffle and the outside wall is 0.125 meters and the froth lip is 0.58 meters from the upper froth baffle. The separation zone is fed through a 0.2 meter diameter duct with a gas-aqueous dispersion containing 0.05 wt % ruptured Dunaliella salina microalgae. The feed rate is 750 liters per minute, and the gas flow rate is 190 liters per minute. The Jg in the separation zone is 0.71 centimeters/second, which shows a high transport rate of collected material from the separation zone into the froth zone. The bubble-particle agglomerates residence time in the separation zone is 117 seconds, while the froth residence time in the froth zone is 390 seconds. The collected froth after collapsing shows a twenty-fold increase in ruptured microalgae concentration.

Example 4

Mineral Recovery

The same pilot-scale flotation cell described in Example 3 is used herein. A 25 wt % aqueous slurry of copper sulfide ore chalcocite ($Cu_2S$) particles with a d80 particle size of 80 microns (i.e., 80% of the particles are less than 80 microns) is fed to the cylindrical separation zone from the central duct. The density of the copper sulfide ore particles is 5.5 g/ml, and the solids contain 0.1% chalcocite. The unfloated solids are discharged through a solids relief line at a solids flow velocity greater than 4 feet/second in order to prevent deposition of the solids and sanding of the line. Thus a high percentage of the total liquid underflow flows through the solids relief valve. The mean residence time of the chalcocite particles in the separation zone is 156 seconds, and the mean residence time of the chalcocite particles in the froth zone is 520 seconds. The chalcocite particles exit in the froth collection launder with 2 wt % chalcocite and a single-pass recovery rate of 65%.

Example 5

Dewatering of an Unruptured Microalgal Dispersion

A commercial-size flotation cell as per Example 3 is constructed. The separation zone is fed through a 0.2 meter diameter duct with an gas-aqueous dispersion containing 0.05 wt % of whole *Dunaliella salina* microalgae together with alum and polymer as is known in the art. The liquid feed rate is 750 liters per minute, and the gas flow rate is 190 liters per minute. The Jg in the separation zone is 0.71 centimeters/second, showing a high transport rate of collected material from the separation zone into the froth zone. The bubble-particle agglomerate residence time in the separation zone is 117 seconds, while the froth residence time in the froth zone is 390 seconds. The collected froth (after collapsing) shows a twenty-fold increase in microalgae concentration.

What is claimed is:

1. A process for concentrating particles in a liquid-particle dispersion by adsorptive bubble separation, the process comprising:
    intimately contacting a gas with the liquid-particle dispersion to form a gas-liquid-particle dispersion;
    introducing the gas-liquid-particle dispersion into a vessel at a point below a surface of a liquid contained therein;
    forming bubbles in the liquid, the bubbles comprising gas-particle agglomerates;
    directing the bubbles to the surface of the liquid with one or more baffles so as to form a floating froth, wherein the froth is enriched in particles and wherein the one or more baffles direct the rising bubbles and falling dislodged particles to the perimeter of the vessel;
    directing the froth towards a froth collection launder in a region of lower surface area than the region where it formed; and
    collecting the froth in the froth collection launder thus collapsing the froth therein and concentrating particles in the liquid-particle dispersion.

2. The process according to claim 1, wherein the collection launder is located substantially in the center of the vessel.

3. The process of claim 1, further comprising:
    removing a portion of the liquid from the collapsed froth, and
    reintroducing the liquid thus removed back into the vessel so as to further collapse the froth being collected in the froth collection launder.

4. The process of claim 1, wherein vacuum is used to pull froth and collapsed froth through the froth collection launder.

5. The process of claim 1, wherein the gas-liquid-particle dispersion is introduced below the surface of the liquid and substantially near the perimeter of the vessel and the froth is collected in a central froth collection launder.

6. The process of claim 4, wherein the vacuum is generated by a pump, compressor, aspirator, venturi, eductor, and/or blower used to provide gas introduced into the vessel.

7. The process of claim 1, wherein the particles comprise microalgae or ruptured microalgae or a combination thereof.

8. The process of claim 7 wherein the microalgae is *Dunaliella*.

9. The process of claim 1, further comprising:
    collapsing the froth in the froth collection launder by the use of chemical defoamers, liquid or gas sprays, vacuum, vibrating objects, spinning objects, sonication, or any combination thereof.

10. The process of claim 1, wherein the particles comprise whole or ruptured microorganisms, whole or ruptured microalgae, droplets of an organic phase, mineral-containing particles, coal particles, biological particles, particles that adhere to a gas-liquid interface, or any combination thereof.

11. The process of claim 1, wherein the particles comprise metals, metal ores, salts, minerals, organic solvents, metal extractants, mineral extractants, oils, solvents, or any combination thereof.

12. A method of adsorptive bubble separation, the method comprising:
    introducing a gas and a liquid-particle dispersion below a surface of a liquid in a mechanical flotation cell or column flotation cell;
    forming bubbles comprising a gas-particle agglomerate;
    directing the bubbles to the surface of the liquid with one or more baffles so as to form a floating froth, wherein the froth is enriched in particles and wherein the one or more baffles direct the rising bubbles and falling dislodged particles to the perimeter of the cell;
    forcing the froth towards a centrally located froth collection launder; and
    collecting the froth by allowing it to overflow into the collection launder.

13. An apparatus for concentrating particles in a liquid-particle dispersion, the apparatus comprising:
    means for intimately contacting a gas with the liquid-particle dispersion to form a gas-liquid-particle dispersion;
    a duct for introducing the gas-liquid-particle dispersion into a flotation vessel at a point below a surface of a liquid contained within the vessel;
    means for directing bubbles to the surface of the liquid so as to form a floating froth thereon, wherein the means for directing the bubbles comprises one or more baffles which direct the rising bubbles and falling dislodged particles to the perimeter of the vessel; and
    means for directing the floating froth towards a froth collection launder in a region of lower surface area than the region where it formed, wherein the froth collection launder collects and removes the froth from the vessel.

14. The apparatus of claim 13, further comprising a pump, compressor, aspirator, venturi, eductor, and/or blower to provide gas introduced into the vessel for preparation of bubbles for froth and for further providing a vacuum to pull froth into the collection launder and/or collapse froth therein.

* * * * *